United States Patent
Zhang et al.

(10) Patent No.: US 11,953,119 B2
(45) Date of Patent: Apr. 9, 2024

(54) MICRO-METERING DEVICE WITH CONSTANT FLOW RATE

(71) Applicant: SHENZHEN KEYTO FLUID TECHNOLOGY CO., LTD., Shenzhen (CN)

(72) Inventors: Cheng Zhang, Shenzhen (CN); Xiyuan Xiao, Shenzhen (CN); Jin Liu, Shenzhen (CN); Yi Wu, Shenzhen (CN)

(73) Assignee: SHENZHEN KEYTO FLUID TECHNOLOGY CO., LTD, Shenzhen (CN)

( * ) Notice: Subject to any disclaimer, the term of this patent is extended or adjusted under 35 U.S.C. 154(b) by 0 days.

(21) Appl. No.: 18/474,975

(22) Filed: Sep. 26, 2023

(65) Prior Publication Data

US 2024/0026992 A1  Jan. 25, 2024

(30) Foreign Application Priority Data

Mar. 15, 2023 (CN) .......................... 202310244164.8

(51) Int. Cl.
*F16K 37/00* (2006.01)
*A61M 5/20* (2006.01)
(Continued)

(52) U.S. Cl.
CPC ............. *F16K 37/005* (2013.01); *A61M 5/20* (2013.01); *A61M 5/31546* (2013.01);
(Continued)

(58) Field of Classification Search
CPC ............... F16K 11/0743; F16K 37/005; F16K 37/0041; F04B 49/065; F04B 49/06;
(Continued)

(56) References Cited

U.S. PATENT DOCUMENTS

| | | | | |
|---|---|---|---|---|
| 3,828,932 A | * | 8/1974 | Schneer | F16K 11/0743 210/411 |
| 6,186,174 B1 | * | 2/2001 | Yurchision | F16K 3/10 137/625.46 |

(Continued)

FOREIGN PATENT DOCUMENTS

| | | |
|---|---|---|
| CN | 203743570 U | 7/2014 |
| CN | 207333824 U | 5/2018 |

(Continued)

*Primary Examiner* — Atif H Chaudry (57) ABSTRACT

A micro-metering device with a constant flow rate, including a rotary shear valve, a mounting seat, a rotation drive assembly, an injection drive assembly and a controller. The rotary shear valve includes a valve main body and a valve spool. The valve main body is provided with a main flow channel and a plurality of branch flow channels. The valve spool is rotatably arranged inside the valve main body, and is configured to communicate the main flow channel with different branch flow channels. A pressure sensor is provided inside the valve main body, and is communicated with the main flow channel. The pressure sensor is configured for detecting a pressure inside the main flow channel. Whether the switching of the liquid path is correct is determined according to the pressure in the main flow channel.

5 Claims, 6 Drawing Sheets

(51) Int. Cl.
*A61M 5/315* (2006.01)
*F04B 17/03* (2006.01)
*F04B 49/06* (2006.01)
*F16K 11/074* (2006.01)
*F16K 31/04* (2006.01)

(52) U.S. Cl.
CPC .... *A61M 5/31565* (2013.01); *A61M 5/31568* (2013.01); *A61M 5/3157* (2013.01); *A61M 5/31576* (2013.01); *A61M 5/31585* (2013.01); *F04B 17/03* (2013.01); *F04B 49/06* (2013.01); *F04B 49/065* (2013.01); *F16K 11/0743* (2013.01); *F16K 31/042* (2013.01); *F16K 37/0041* (2013.01); *A61M 5/31573* (2013.01); *A61M 2005/31588* (2013.01); *F04B 2201/0201* (2013.01); *F04B 2205/03* (2013.01)

(58) Field of Classification Search
CPC ............... F04B 17/03; F04B 2205/03; F04B 2201/0201; A61M 5/20; A61M 5/31546; A61M 5/31565; A61M 5/3157; A61M 5/31568; A61M 5/31576; A61M 5/31585; A61M 2005/31588; A61M 5/31573
See application file for complete search history.

(56) References Cited

U.S. PATENT DOCUMENTS

| | | | |
|---|---|---|---|
| 2003/0167039 A1* | 9/2003 | Moberg | A61M 5/1456 604/135 |
| 2014/0076992 A1* | 3/2014 | Cooper | B05B 9/0413 239/73 |
| 2019/0234399 A1 | 8/2019 | Karunaratne et al. | |

FOREIGN PATENT DOCUMENTS

| | | |
|---|---|---|
| CN | 112483679 A | 3/2021 |
| CN | 112555211 A | 3/2021 |
| CN | 112577532 A | 3/2021 |
| CN | 113236820 A | 8/2021 |
| CN | 214035995 U | 8/2021 |
| CN | 214788053 U | 11/2021 |
| CN | 115671443 A | 2/2023 |

* cited by examiner

MICRO-METERING DEVICE WITH CONSTANT FLOW RATE

CROSS-REFERENCE TO RELATED APPLICATIONS

This application claims the benefit of priority from Chinese Patent Application No. 202310244164.8, filed on Mar. 15, 2023. The content of the aforementioned application, including any intervening amendments thereto, is incorporated herein by reference in its entirety.

TECHNICAL FIELD

This application relates to hydraulic systems, and more particularly to a micro-metering device with a constant flow rate.

BACKGROUND

The commercially-available syringe pump products equipped with a rotary shear valve all use a syringe as a power source, and can achieve the liquid transfer among multiple branches by switching the liquid path of the rotary shear valve. For example, Chinese Patent Application No. 202011298802.7 discloses a syringe device with a rotary shear valve.

In most cases, it is required to ensure a high pressure stability when there are liquids flowing in the liquid paths of the rotary shear valve, and the micro-volume and low-speed liquid discharge is often used. To monitor the pressure or flow rate of the liquid flowing in the liquid paths of the rotary shear valve, it is often required to introduce pressure or flow sensors at the outlets of individual liquid paths to detect pressure fluctuation or flow change in each liquid path, where the sensors generally require high accuracy. Such methods at least have the following shortcomings:

(1) Additional pipelines are required for connecting the sensors, such that the number of locations where sealing is required is increased. Furthermore, the extension of the pipeline results in a larger chamber volume in the pipeline, which may affect the injection accuracy for those applications that require accurate dosing.

(2) It requires additional spaces for the sensor installation, which is not suitable for the products having high requirements for the overall size and will result in high costs.

(3) When the switching of the liquid path of the rotary shear valve is incorrect or the liquid path is in a half-open and half-closed state, as the sensor is arranged outside the output end of the rotary shear valve, and there is no pressure on the input end for comparative reference, the sensor is unable to detect effective pressure fluctuations, and thus fails to determine whether the switching of the liquid path is correct. In the case of incorrect switching of the liquid path, the syringe may suffer an explosion due to an excessive pressure during the liquid suction and discharge.

(4) The sensors are arranged at the periphery of the syringe pump, and therefore cannot form an absolute closed-loop control loop with the syringe pump. When the sensor detects abnormal pressure fluctuations, the syringe pump cannot be adjusted in time, especially for the micro-volume application (e.g., nL level). Hence, the current syringe pump cannot satisfy the high-precision liquid discharge, and cannot ensure the timely pressure correction, thereby affecting the accuracy of liquid suction and discharge.

SUMMARY

An objective of the present disclosure is to provide a micro-metering device with a constant flow rate to overcome the deficiencies of inconvenient sensor installation, high cost and inability to effectively monitor pressure fluctuations in liquid paths in the existing syringe pump products having a rotary shear valve.

The technical solutions of the present disclosure will be described below.

This application provides a micro-metering device with a constant flow rate, comprising:
  a rotary shear valve;
  wherein the rotary shear valve comprises a valve main body and a valve spool; the valve main body is provided with a main flow channel and a plurality of branch flow channels; and the valve spool is rotatably arranged inside the valve main body, and is configured to communicate the main flow channel with at least one of the plurality of branch flow channels; and
  a pressure sensor is provided inside the valve main body, and is communicated with the main flow channel; and the pressure sensor is configured for detecting a pressure inside the main flow channel.

In some embodiments, the valve main body comprises a valve head cover, a valve head and a valve head housing arranged sequentially from one side to the other side, wherein the main flow channel and the plurality of branch flow channels are provided on the valve head;
  a first side of the valve head is provided with a mounting groove communicated with the main flow channel, and the mounting groove is configured to accommodate the pressure sensor; a sealing ring is provided between a first side of the pressure sensor and the mounting groove; and the valve head cover is configured to seal the mounting groove, and is detachably connected to the valve head;
  a lead wire of the pressure sensor is connected with a probe; and the probe passes through the valve head and the valve head housing successively and extends to an outside of the valve head housing; and
  the valve spool is rotatably arranged in an inner cavity of the valve head housing, and is located on a second side of the valve head; and a valve body is arranged between the valve head and the valve spool.

In some embodiments, a valve spool base, a bearing and a disc spring are provided insequence in the inner cavity of the valve head housing from one side to the other side; the valve spool base is rotatably provided in the inner cavity of the valve head housing via the bearing; the valve spool is fixedly arranged on a first side of the valve spool base; a sealing gasket is provided between the valve spool and the valve spool base; a connection port is provided on a second side of the valve spool base, and a through hole aligned with the connection port is provided on a side of the valve head housing; and a first end of the disc spring is connected to the bearing, and a second end of the disc spring is connected to the valve head housing.

In some embodiments, a side of the valve head cover is provided with an abutting step; a side of the abutting step abuts against a second side of the pressure sensor; and the abutting step is provided with a notch for the lead wire of the pressure sensor to pass through.

In some embodiments, the micro-metering device further comprises a mounting seat, a rotation drive assembly, an injection drive assembly and a controller; the rotary shear valve is arranged on one side of the mounting seat, and the rotation drive assembly, the injection drive assembly and the controller are arranged on the other side of the mounting seat; and the rotation drive assembly is configured to drive the valve spool to rotate; the injection drive assembly comprises an injector and an injection drive member; an output end of the injector is communicated with the main flow channel; the injection drive member is configured to drive the injector to realize suction and discharge of the liquid; and the pressure sensor, the rotation drive assembly and the injection drive assembly are electrically connected to the controller.

In some embodiments, the rotation drive assembly comprises a rotation drive motor, a rotary shaft, a zero-position code disk, a positioning code disk and a rotary photoelectric sensor;

wherein the rotation drive motor is fixedly arranged on the side of the mounting seating away from the rotary shear valve; one end of the rotary shaft is in transmission connection with the rotation drive motor, and the other end of the rotary shaft is in transmission connection with the valve spool; the zero-position code disk and the positioning code disk are both sleeved on an outer wall of the rotary shaft and are coaxial with the rotary shaft; the rotary photoelectric sensor is arranged on a side of the rotary shaft, and is adapted to the zero-position code disk and the positioning code disk; and the rotation drive motor the rotary photoelectric sensor are electrically connected to the controller.

In some embodiments, the injection drive member comprises an injection drive motor, a transmission component, a ball screw, a push plate and a linear encoder; the ball screw is rotatably arranged on a side of the mounting seat back away from the ball screw; the injection drive motor is in transmission connection with the ball screw through the transmission component, so that the ball screw is driven by the injection drive motor to rotate; the ball screw runs through the push plate and is threadedly connected to the push plate; the push plate is capable of sliding along an axial direction of the ball screw; the mounting seat is provided with an avoidance opening adapted to the push plate; the input end of the injector is connected to the push plate; the linear encoder is configured to detect a position of the push plate; and the injection drive motor and the linear encoder are electrically connected to the controller.

In some embodiments, the transmission component comprises a drive wheel, a driven wheel and a synchronous belt; the drive wheel is in transmission connection with an output end of the injection drive motor; the driven wheel is sleeved on an outer wall of the ball screw and is coaxial with the ball screw; and the drive wheel and the driven wheel are in transmission connection through the synchronous belt.

In some embodiments, the linear encoder comprises a ruler bar and a read head assembly; the ruler bar is fixedly provided on the push plate, and is parallel to the ball screw; the read head assembly is fixedly provided on the mounting base, and is electrically connected to the controller.

In some embodiments, the injection drive member comprises two guide columns; the two guide columns are symmetrically arranged on two sides of the ball screw and are parallel to the ball screw; and each of the two guide columns runs through the push plate and is slidably connected to the push plate.

Compared to the prior art, this application has the following beneficial effects.

(1) In the metering device provided herein, the pressure sensor is provided inside the main body of the rotary shear valve to detect the pressure in the main flow channel, so as to determine whether the liquid path is switched correctly. Compared with the manner in which branch flow channels are each provided with a sensor, it reduces the cost and the installation space. Meanwhile, the sensor can cooperate with the controller and the rotation drive assembly to form a closed-loop control. When the pressure detected by the pressure sensor is not within the preset range, the rotation drive assembly can be controlled in time by the controller to drive the valve spool of the rotary shear valve to rotate by a corresponding angle to ensure the correct switching of the liquid path. Therefore, the design proposed herein can effectively reduce the risks of insufficient flow caused by incorrect liquid path switching, diminish the overall size, and improve the operation reliability of the device.

(2) By arranging the pressure sensor to detect the pressure in the main flow channel, in the liquid suction and discharge, when the pressure sensor detects a large pressure fluctuation in the main flow channel, the output power of the injection drive motor can be promptly adjusted through the controller to maintain the pressure within a normal range, thereby ensuring the pressure stability at the output end of the rotary shear valve and improving the precision of the liquid suction and discharge.

(3) In this application, the ball screw is used as the transmission component to cooperate with the linear encoder to avoid desynchronization, which can make the resolution of the injection drive motor reach 1000 or even higher for one revolution. When the amount of liquid during the suction and discharge is extremely small, due to the improved resolution, it can still effectively avoid the desynchronization to ensure the accuracy of the suction and discharging of liquid in an extremely micro volume. In addition, since the code rail of the linear encoder is fixedly arranged on the push plate, it can prevent the failure of the desynchronization-avoiding function of the injection drive motor when the synchronous belt becomes slack.

(4) In this application, the transmission component including the drive wheel, the driven wheel and the synchronous belt is adopted. In practice, it is only necessary to modify the gear ratio between the drive wheel and the driven wheel to reach the high-speed high-flow or low-speed low-flow suction and discharge. Compared with the use of the motor to directly drive the rotation of the screw, the transmission component can further expand the application range of the metering device in the suction and discharge of liquids.

In the drawings: 10, mounting seat; 20, rotary shear valve; 21, valve spool; 22, pressure sensor; 23, valve head cover; 24, valve head; 25, valve head housing; 26, sealing ring; 27, probe; 28, valve body; 29, valve spool base; 210, bearing; 211, disc spring; 212, sealing gasket; 30, rotation drive assembly; 31, rotary mounting bracket; 32, rotation drive motor; 33, rotary shaft; 34, zero-position code disk; 35, positioning code disk; 36, rotary photoelectric sensor; 40, injection drive assembly; 41, injector; 411, injection cylinder; 412, injection piston; 42, injection drive member; 421, injection mounting bracket; 422, injection drive motor; 423, ball screw; 424, push plate; 425, linear encoder; 4251, code rail; 4252, read head assembly; 426, drive wheel; 427, driven wheel; 428, synchronous belt; 429, guide column; 50, controller; a, main flow channel; b, branch flow channel; and c, transition flow channel.

DETAILED DESCRIPTION OF EMBODIMENTS

Referring to FIGS. 1-6, a micro-metering device with a constant flow rate is provided to overcome at least the following technical problems of the existing rotary shear valve-equipped syringe pump products: inconvenient sensor installation, high cost, and inability to effectively monitor pressure fluctuation in the liquid path. Specifically, the metering device includes a mounting seat 10, a rotary shear valve 20, a rotation drive assembly 30, an injection drive assembly 40, and a controller 50.

Figure 1:
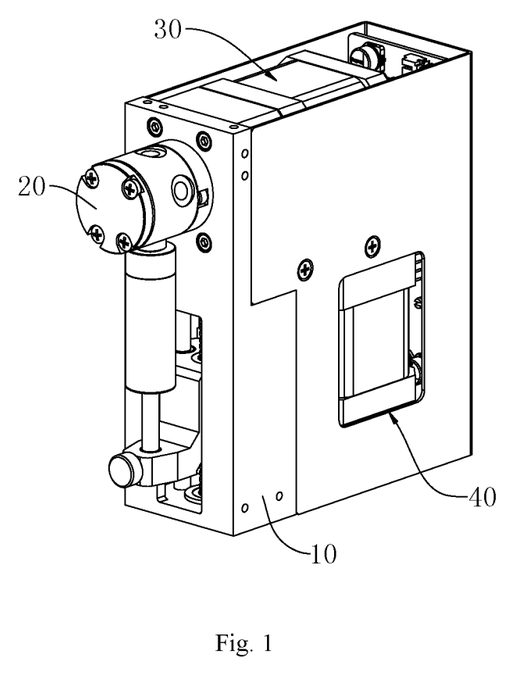
FIG. 1 is a schematic structural diagram of a micro-metering device with a constant flow rate according to an embodiment of the present disclosure.
Figure 2:
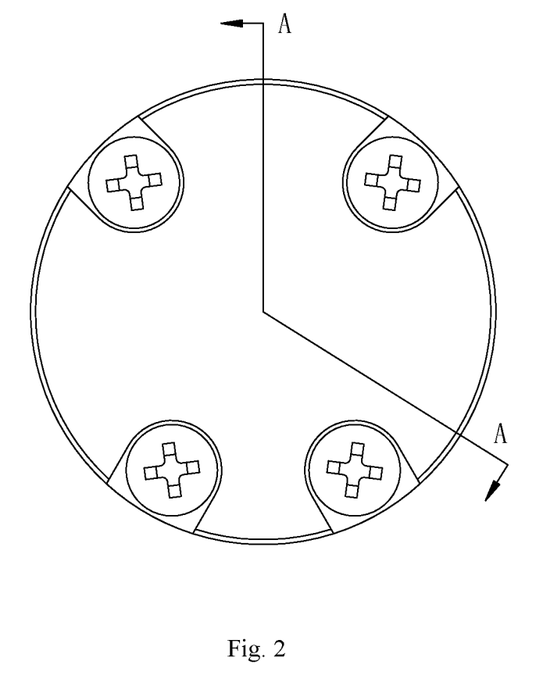
FIG. 2 is a side elevational view of a rotary shear valve according to an embodiment of the present disclosure.

In this embodiment, the mounting seat 10 serves as a support body of the metering device, and the rotary shear valve 20, the rotation drive assembly 30, the injection drive assembly 40 and the controller 50 are all fixedly mounted on the mounting seat 10. Specifically, as shown in FIG. 1, the rotary shear valve 20 is arranged on one side of the mounting seat 10, and the rotation drive assembly 30, the injection drive assembly 40 and the controller 50 are arranged on the other side of the mounting seat 10. In practical implementation, a housing may be provided on the side of the mounting seat 10 away from the rotary shear valve 20 to protect the rotation drive assembly 30, the injection drive assembly 40, and the controller 50.

In this embodiment, the rotary shear valve 20 is configured to realize the switching of different liquid paths. Specifically, referring to FIG. 3, the rotary shear valve 20 includes a valve main body 28, a valve spool 21 and a pressure sensor 22. The valve main body has a main flow channel a and a plurality of branch flow channels b. The valve spool 21 is rotatably arranged inside the valve main body and is provided with a transition flow channel c. One end of the transition flow channel c is always communicated with the main flow channel a, and the other end of the transition flow channel c is capable of being communicated with different branch flow channels b. Specifically, when the valve spool 21 is rotated, the main flow channel a can be communicated with different branch flow channels b through the transition flow channel c, so as to realize the switching of the liquid path.

Figure 3:
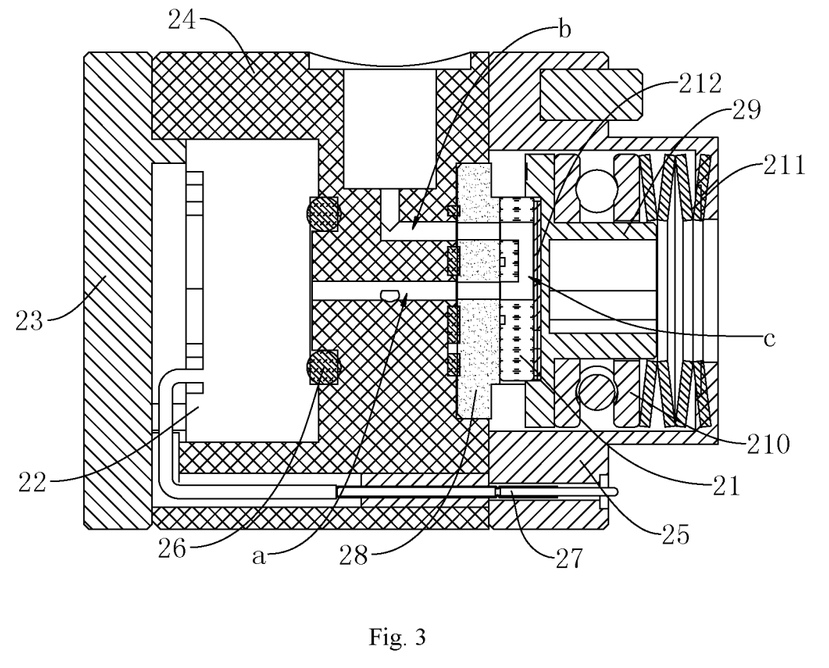
FIG. 3 is a sectional view of the rotary shear valve along A-A line in FIG. 2.
Figure 4:
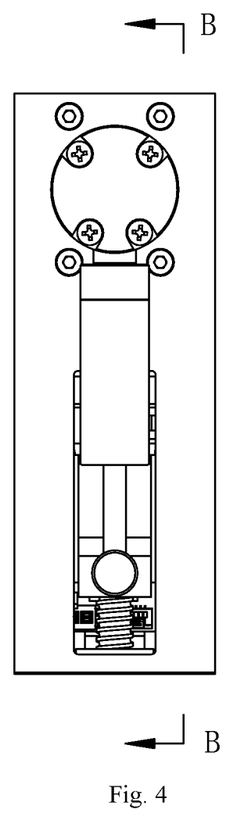
FIG. 4 is a side elevational view of the micro-metering device according to an embodiment of the present disclosure.

At this time, to monitor whether the liquid path is switched correctly, as shown in FIG. 3, a pressure sensor 22 is provided inside the valve main body and is communicated with the main flow channel a. The pressure sensor 22 is configured for detecting the pressure inside the main flow channel a. At this time, the pressure sensor 22 is electrically connected to the controller 50 to transmit the detected pressure information to the controller 50. Since the pressure inside the main flow channel a when the main flow channel a is completely communicated with a corresponding branch flow channel b is different from the pressure inside the main flow channel a when the main flow channel a is incompletely or not communicated with the corresponding branch flow channel b, it is possible to determine whether the main flow channel a and the corresponding branch channel b are completely communicated by detecting the pressure inside the main flow channel a and comparing the detected pressure with a preset range of pressures through the controller 50, so that whether the fluid path is switched correctly can be determined.

Therefore, in this embodiment, by setting the pressure sensor 22 inside the valve main body for detecting the pressure inside the main flow channel a, whether the liquid path is switched correctly can be determined through the pressure inside the main flow channel a. This reduces the cost and saves the space for installing sensors compared with setting a sensor inside each branch flow channel b. Moreover, it also reduces the risk of small liquid path and insufficient flow caused by incorrect liquid path switching, saves the overall size of the device, and improves the reliability of the device during operation.

It can be understood that the above pressure sensor 22 may also be replaced with a flow sensor in actual implementation. The flow sensor detects flow information inside the main flow channel a and converts the flow information into an approximate pressure, so as to achieve the same function as the pressure sensor 22, i.e., to determine whether the main flow channel a is fully communicated with the corresponding branch flow channel b.

To install the pressure sensor 22, as shown in FIG. 3, the valve main body in the present embodiment includes a valve head cover 23, a valve head 24, and a valve head housing 25 arranged sequentially from left to right, where the main flow channel a and the plurality of branch flow channels b are provided on the valve head 24. Exemplarily, the main flow channel a is provided at the center of an interior of the valve head 24, and the plurality of branch flow channels b are uniformly arranged along the circumference of the valve head 24.

At this time, referring to FIG. 3, the left side of the valve head 24 is provided with a mounting groove connected to the main flow channel a, and the pressure sensor 22 is received in the mounting groove for detecting the pressure inside the main flow channel a through the pressure sensor 22. A sealing ring 26 is provided between the right side of the pressure sensor 22 and the mounting groove, and is provided around the main flow channel a to realize reliable sealing between the pressure sensor 22 and the main flow channel a, thus avoiding liquid from flowing out of the gap between the valve head 24 and the pressure sensor 22. The valve head cover 23 is configured to seal the mounting groove on the left side of the valve head 24, and is detachably connected to the valve head 24. By arranging the pressure sensor 22 in the mounting groove in combination with the detachable valve head cover 23, it is conducive to the quick disassembly of the pressure sensor 22, thereby facilitating the replacement the pressure sensor 22 or the valve head 24 in the later.

It can be understood that, to improve the stability of the pressure sensor 22 after installed in place, referring to FIG. 3, the right side of the valve head cover 23 is provided with an abutting step. The right side of the abutting step abuts against the left side of the pressure sensor 22 to press the pressure sensor 22 against the mounting groove. At the same time, to facilitate the electrical connection between the pressure sensor 22 and the controller 50 and the replacement of the valve head 24, a lead wire of the pressure sensor 22 is also connected with a probe 27, and the probe 27 passes through the valve head 24 and the valve head housing 25 successively and extends to the outside of the valve head housing 25. When it requires to electrically connect the pressure sensor 22 with the controller 50, it is necessary to connect the probe 27 to the controller 50 using a cable. And at this time, the abutting step is provided with a notch for the lead wire of the pressure sensor 22 to pass through, so as to facilitate the lead wire of the pressure sensor 22 to be connected to the probe 27 after passing through the notch.

As shown in FIG. 3, the valve spool 21 is rotatably arranged in an inner cavity of the valve head housing 25, and is located on the right side of the valve head 24. A valve body 28 is arranged between the valve head 24 and the valve spool 21. Specifically, a valve spool base 29, a bearing 210 and a disc spring 211 are provided insequence in the inner cavity of the valve head housing 25 from left to right, and the valve spool base 29 is rotatably provided in the inner cavity of the valve head housing 25 via the bearing 210. The valve spool 21 is fixedly arranged on the left side of the valve spool base 29, and a sealing gasket 212 is provided between the valve spool 21 and the valve spool base 29 to ensure a good sealing performance between the valve spool 21 and the valve spool base 29, thus avoiding the liquid in the transition flow channel c from flowing out of the gap between the valve spool 21 and the valve spool base 29. In the meanwhile, a connection port is provided on the right side of the valve spool base 29, and a through hole aligned with the connection port is provided on the right side of the valve head housing 25, so as to facilitate the transmission connection between the output end of the rotation drive assembly 30 and the valve spool base 29, thereby driving the valve spool base 29 together with the valve spool 21 to synchronously rotate through the rotation drive assembly 30 to achieve the switching of the liquid paths. The disc spring 211 is configured for buffering and damping. Specifically, one end of the disc spring 211 is connected to the bearing 210, and the other end of the disc spring 211 is connected to the valve head housing 25.

In this embodiment, the rotation drive assembly 30 is configured to drive the valve spool 21 to rotate. Specifically, the rotation drive assembly 30 is configured to drive the valve spool base 29 to rotate, so as to drive the valve spool 21 to rotate synchronously, and thus realizing the switching of different liquid paths of the rotary shear valve 20. At the same time, the rotation drive assembly 30 is electrically connected to the controller 50 to automatically control the rotation angle of the spool base 29 by the controller 50, thereby facilitating the accurate conduction of the main flow channel a and the corresponding branch flow channel b, and improving the accuracy of the switching of different liquid paths.

Figure 5:
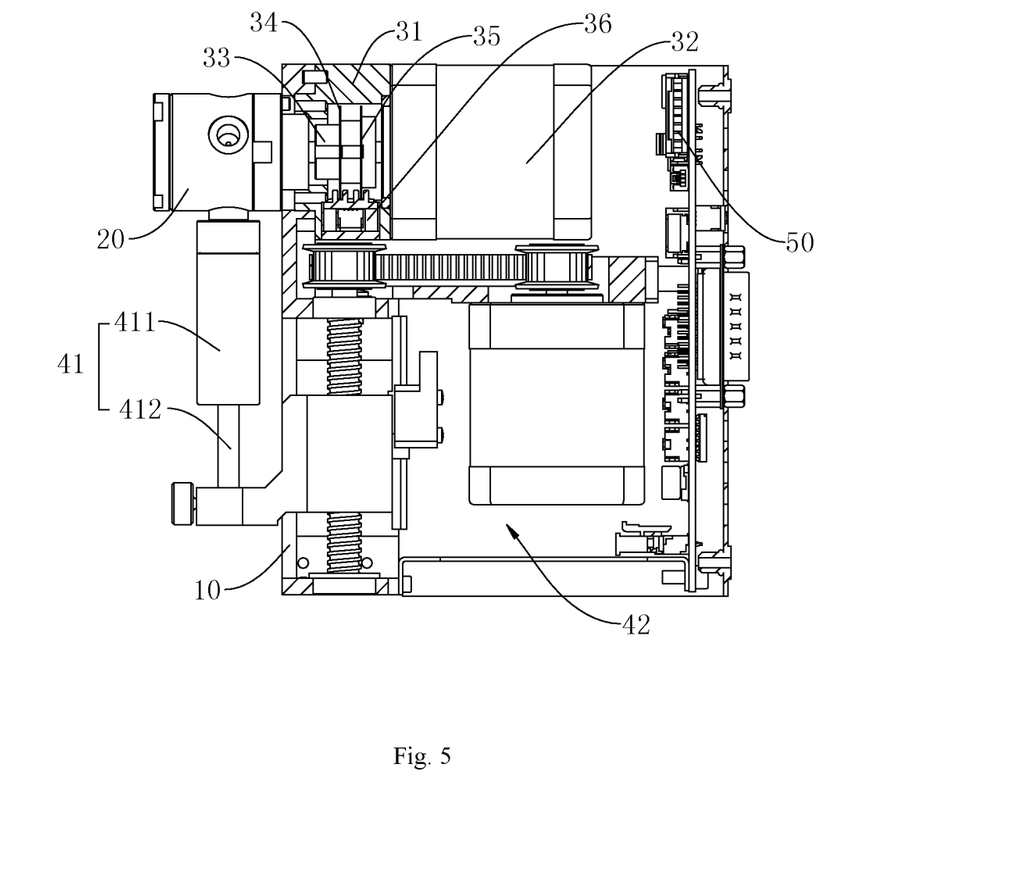
FIG. 5 is a sectional view of the micro-metering device along B-B line in FIG. 4.

Specifically, as shown in FIG. 5, the rotation drive assembly 30 includes a rotary mounting bracket 31, a rotation drive motor 32, a rotary shaft 33, a zero-position code disk 34, a positioning code disk 35 and a rotary photoelectric sensor 36, where the rotary mounting bracket 31 is fixedly arranged on the side of the mounting seat 10 away from the rotary shear valve 20, and the rotation drive motor 32 is fixedly arranged on the rotary mounting bracket 31 such that the rotation drive motor 32 is fixedly arranged on the side of the mounting seating 10 away from the rotary shear valve 20. The rotation drive motor 32 is electrically connected to the controller 50 such that the rotation drive motor 32 is controlled by the controller 50 to work. At this time, one end of the rotary shaft 33 is in transmission connection with the rotation drive motor 32 such that the rotary shaft 33 is driven by the rotation drive motor 32 to rotate, and the other end of the rotary shaft 33 is in transmission connection with the valve spool 21. Specifically, the rotary shaft 33 passes through the through hole of the valve head housing 25 and then extends to the connection port of the valve spool base 29 to be connected to the valve spool base 29. When the rotation drive motor 32 drives the rotary shaft 33 to rotate, the rotary shaft 33 will drive the valve spool base 29 and the valve spool 21 to rotate synchronously, thereby realizing the switching of the different liquid paths.

As shown in FIG. 5, the zero-position code disk 34 and the positioning code disk are both sleeved on an outer wall of the rotary shaft 33 and are coaxial with the rotary shaft 33, and the rotary photoelectric sensor 36 is arranged on a side of the rotary shaft 33. Specifically, the rotary photoelectric sensor 36 is fixedly arranged on the rotary mounting bracket 31, and is adapted with the zero-position code disk 34 and the positioning code disk 35. And at this time, the rotary photoelectric sensor 36 is electrically connected to the controller 50. During operation, the rotary photoelectric sensor 36 identifies the position of the rotary shaft 33 through the zero-position code disk 34 and the positioning code disk 35, and transmits the identified position information to the controller 50 so as to facilitate the controller 50 in controlling the rotation drive motor 32 to work, thereby allowing the rotary shaft 33 to drive the valve spool base 29 and the valve spool 21 to synchronously rotate at a certain angle to realize the switching of different liquid paths. In this embodiment, the positioning code disk 35 with higher precision is introduced, which is conducive to improving the switching precision of different liquid paths.

In this embodiment, as shown in FIG. 5, the injection drive assembly 40 includes an injector 41 and an injection drive member 42. The injector 41 is provided on the same side as the rotary shear valve 20, and an output end of the injector 41 is connected to the main flow channel a. The injection drive member 42 is configured to drive the injector 41 to realize suction and discharge of the liquid. Specifically, the injector 41 includes an injection cylinder 411 and an injection piston 412. An injection channel (not shown in the figures) is provided in the valve head 24. One end of the injection cylinder 411 is configured as the output end and is connected to the middle of the main flow channel a through the injection channel. The injection piston 412 is slidably provided inside the injection cylinder 411, and a fixed end of the injection piston 412 passes through the other end of the injection cylinder 411 and then extends to the outside of the injection cylinder 411 to be connected to the output end of the injection drive member 42, so as to drive the injection piston 412 to slide inside the injection cylinder 411 through the injection drive member 42, thereby realizing suction and discharge of liquid.

The injection drive member 42 is electrically connected to the controller 50 such that the injection drive member 42 is driven by the controller 50 to work, thereby realizing precise control of the amount of liquid during suction and discharge. Specifically, referring to FIGS. 5 and 6, the injection drive member 42 includes an injection mounting bracket 421, an injection drive motor 422, a transmission component, a ball screw 423, a push plate 424 and a linear encoder 425. The injection mounting bracket 421 is provided on the side of the mounting seat 10 back from the rotary shear valve 20, and the injection drive motor 422 is fixedly arranged on the injection mounting bracket 421. At this time, the ball screw 423 is rotatably and perpendicularly arranged on the side of the mounting seat 10 back away from the rotary shear valve 20. The injection drive motor 422 is in transmission connection with the ball screw 423 through the transmission component, so that the ball screw 423 is driven by the injection drive motor 422 to rotate.

Figure 6:
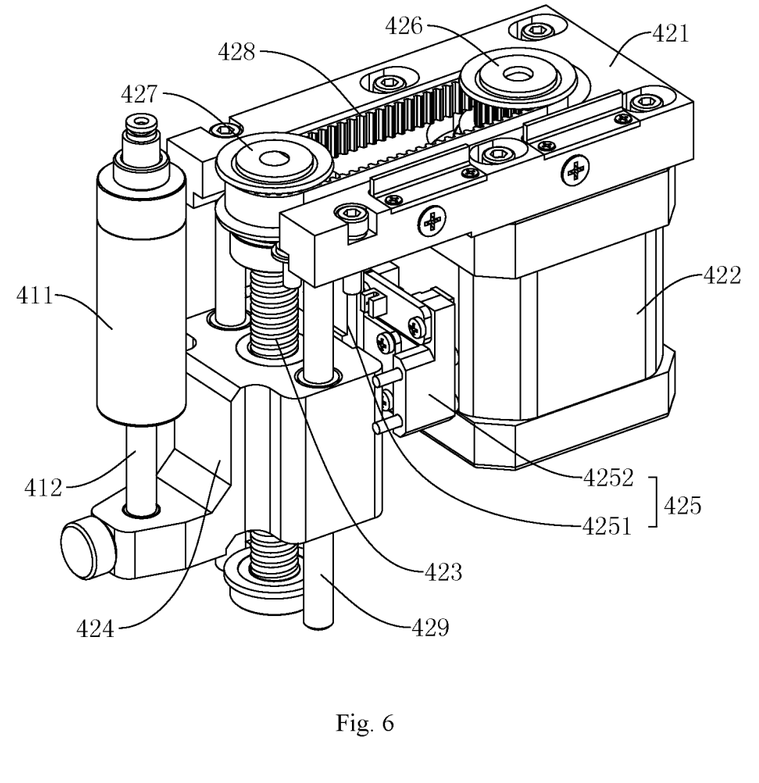
FIG. 6 is a schematic structural diagram of an injection drive assembly according to an embodiment of the present disclosure.

At the same time, the ball screw 423 runs through the push plate 424 and is threadedly connected to the push plate 424. The push plate 424 can slide along the axial direction of the ball screw 423. The mounting seat 10 is provided with an avoidance opening adapted to the push plate 424 to prevent interference between the push plate 424 and the mounting seat 10 when the push plate 424 is moving. At this time, the input end of the injector 41 is connected to the push plate 424. Specifically, the fixed end of the injection piston 412 is connected to the push plate 424, and is electrically connected to the controller 50. The linear encoder 425 includes a ruler bar 4251 and a read head assembly 4252. The ruler bar 4251 is fixedly provided on the push plate 424 and is parallel to the ball screw 423. The read head assembly 4252 is fixedly provided on the mounting base 10, and is electrically connected to the controller 50. The position of the push plate 424 on the ball screw 423 can be obtained through the reading head assembly 4252 in cooperation with the ruler bar 4251, which is conducive to the controller 50 controlling the injection drive motor 422 to work according to the position of the push plate 424, thereby controlling the movement stroke of the push plate 424 to achieve precise suction and discharge of the liquid.

By such arrangements, in actual use, the injection drive motor 422 drives the ball screw 423 to work, at which time the rotation movement of the ball screw 423 will be transformed into the linear movement of the push plate 424 along the axial direction of the ball screw 423. In this case, by driving the injection piston 412 to move through the push plate 424, in combination with the linear encoder 425 to detect the position of the push plate 424 in real time, the amount of liquid during suction and discharge can be precisely controlled.

It should be noted that the ball screw 423 is used as the transmission component which is in cooperation with the linear encoder 425, so that the actual movement of the injection piston 412 can be timely and accurately feedback to the controller 50, thereby timely calibrating the position of the push plate 424 through the controller 50 to improve the precision of the suction and discharge of the liquid. Compared with the conventional trapezoidal screw, the ball screw 423 has a smaller coefficient of friction, and due to the zero clearance characteristics of the ball screw 423, there is no need to eliminate the back clearance in actual use. Thus, the ball screw 423 has a higher transmission efficiency and can meet the demand for high-speed suction and discharge. Moreover, as the ruler bar 4251 of the linear encoder 425 is in rigid connection with the push plate 424, the resolution of the linear encoder 425 can be effectively improved to reach 1000 or even higher, so as to satisfy the requirement of suction and discharge of very small micro-volume of liquid.

Referring to FIGS. 5 and 6, the transmission component in this embodiment includes a drive wheel 426, a driven wheel 427 and a synchronous belt 428, where the drive wheel 426 is in transmission connection with the output end of the injection drive motor 422 such that the drive wheel 426 is driven by thee injection drive motor 422 to rotate. The driven wheel 427 is sleeved on the outer wall of the ball screw 423 and is coaxial with the ball screw 423 to allow the driven wheel 427 to rotate coaxially with the ball screw 423. The drive wheel 426 and the driven wheel 427 are connected in a transmission manner through the synchronous belt 428. When the injection drive motor 422 drives the driven wheel 426 to rotate, the ball screw 423 will start to rotate under the coordinated transmission effect of the synchronous belt 428 and the driven wheel 427. At this time, it is only necessary to modify the number of teeth of the transmission ratio between the drive wheel 426 and the driven wheel 427, the high-speed high flow or low-speed low-flow suction and discharge can be realized. Compared with the use of the motor to directly drive the rotation of the screw, as the motor cannot directly drive the screw to rotate at high speeds, the transmission component consisting of the drive wheel 426, the driven wheel 427 and the synchronous belt 428 can further expand the application range of the dosing device in the suction and discharge of liquids.

It should be noted that, in actual implementation, the drive wheel 426, the driven wheel 427 and the synchronous belt 428 in the above-described transmission component can also be replaced by conventional transmission components (such as sprocket chains, pulley belts, and gears), and the above-described functions can also be realized.

In addition, to improve the stability of the push plate 424 when it moves in a straight line along the axial direction of the ball screw 423, as shown in FIG. 6, the injection drive member 42 also includes two guide columns 429. The two guide columns 429 are symmetrically arranged on two sides of the ball screw 423 and are parallel to the ball screw 423. Each of the two guide columns 429 runs through the push plate 424 and is slidably connected to the push plate 424. When the push plate 424 moves in a straight line along the axial direction of the ball screw 423, the push plate 424 will synchronously slide along the axial direction of the guide column 429, so that the two guide columns 429 are configured to play a good role in limiting and guiding.

To more clearly and intuitively understand the dosing device provided in this embodiment, the working principles of the dosing device will be further elaborated below.

In practice, the controller 50 is communicatively connected to a corresponding upper computer such that corresponding control instructions can be sent to the controller 50 via the upper computer.

When the controller 50 receives the liquid path switching instruction sent by the upper computer, the controller 50 controls the rotation drive motor 32 to work. At this time, the rotation drive motor 32 drives the rotary shaft 33 to rotate to drive the valve spool base 29 and the valve spool 21 to rotate synchronously through the rotary shaft 33. During this process, the rotary photoelectric sensor 36, the zero-position code disk 34, and the positioning code disk 35 together serve as a closed-loop detection to detect the rotation angle of the rotary shaft 33 in real time, so as to ensure that the liquid path is switched correctly.

Moreover, the rotation drive motor 32 stops when the liquid path switching is completed. The controller 50 controls the injection drive motor 422 to work to carry out a small-amplitude suction and discharge test, during which the pressure sensor 22 detects the pressure in the main flow channel a in real time and transmits the detected pressure to the controller 50. The controller 50 compares the received pressure with the preset pressure range to further determine whether the liquid path is switched correctly. Specifically, if the pressure received by the controller 50 is within the preset pressure range, it indicates that the liquid path is correctly switched, and conversely, if the pressure received by the controller 50 is not within the preset pressure range (usually the pressure is less than the preset pressure range), the controller 50 again controls the rotation drive motor 32 to work to slightly adjust the rotation angle of the valve spool 21 until the pressure sensor 22 detects that the pressure is within the preset pressure range.

In the suction and discharge phase, when the controller 50 receives the suction and discharge instruction from the upper computer, the controller 50 drives the injection drive motor 422 to work, at which time, the ball screw 423 starts to rotate under the transmission action of the drive wheel 426, the driven wheel 427 and the synchronous belt 428, and the push plate 424 makes a straight-line movement along the axial direction of the ball screw 423 to drive the injection piston 412 to move synchronously, thereby realizing the suction and discharge of liquid. In this process, the linear encoder 425 can detect the position of the push plate 424 on the ball screw 423 in real time, to ensure the good precision of the suction and discharge of liquid. In the meanwhile, the pressure sensor 22 continues to detect the pressure in the main flow channel a. If the pressure fluctuation is large in the main flow channel a, then the controller 50 dynamically modifies the output power of the injection drive motor 422 to ensure that the pressure of the liquid ultimately flowing out of the corresponding branch channel b is stable. In this case, the liquid in the liquid path of the rotary shear valve 20 can flow at a specified flow rate during the suction and discharge phase, which further improves the precision of the suction and discharge of the liquid.

In summary, in the dosing device provided in this embodiment, the pressure sensor 22 is directly provided inside the valve head 24 on the basis of the existing rotary shear valve 20 to detect the pressure in the main flow channel a. In this case, there is no need to separately arrange the corresponding sensors in each branch flow channel b to realize the detection of pressure fluctuation in different liquid paths, which saves the installation space while reduces the cost, realizes the detection of whether the liquid paths are switched correctly, and avoids the situation that the liquid path is incorrectly switched or the main flow channel a and the corresponding branch flow channel b are in a half-open and half-closed state after switching. Furthermore, in the suction and discharge phase, when the pressure sensor 22 detects a large fluctuation of the pressure in the main flow channel a, it can promptly adjust the output power of the injection drive motor 422 through the controller 50 to ensure the smoothness of the pressure in the main flow channel a.

Moreover, in the present embodiment, the ball screw 423 is used as the transmission component and is in cooperation with the linear encoder 425 to avoid desynchronizing, the accuracy of which can make the resolution of the injection drive motor 422 reach 1000 or even higher when it rotates one round. When the amount of liquid during the suction and discharge is extremely small, due to the improved resolution, it can still play the role in avoiding desynchronizing to ensure the accuracy of the suction and discharging of liquid in an extremely micro volume. In addition, since the ruler bar 4251 of the linear encoder 425 is fixedly arranged on the push plate 424, the failure of the desynchronizing-avoiding function of the injection drive motor 422 is avoided when the synchronous belt 428 becomes slack.

It should be noted that a corresponding alarm module (e.g., an alarm) can also be introduced in the actual implementation, which is electrically connected to the controller 50. In this case, in the actual application, when the liquid path is incorrectly switched or the pressure in the main flow channel a fluctuates greatly during suction and discharge of the liquid, the controller 50 is capable of controlling the alarm module to issue a warning signal in time to remind the relevant staff to make a timely response.

In addition, considering that the injection cylinder 411 is generally made of glass, and the injection piston 412 is generally made of a plastic material, repeated friction will occur between the injection piston 412 and the injection cylinder in practice 411, which will shorten the service life of the injection cylinder 411, such that the injection cylinder 411 needs to be replaced frequently.

To facilitate the replacement of the injection cylinder 411, a reset button (not shown in the drawings) in communication connection with the controller 50 may also be added in practice. When the reset button is pressed, the reset button can send a reset signal to the controller 50, and the controller 50 can respond to the reset signal to control the injection drive motor 422 to work, so that the push plate 424 drives the injection piston 412 to move to the reset position, thereby facilitating the disassembly of the injector 41 (namely, separating the injection piston 412 from the injection cylinder 411), and the replacement of the injection cylinder 411.

The reset position refers to the limit position of the downward movement of the push plate 424. In the actual implementation, the reset button may be arranged as needed, for example, it may be located at an outer side wall of the mounting seat 10.

At the same time, the above reset button can be a button with different colored indicators, so that in the actual application, the controller 50 can control the indicator lights of different colors of the reset button to light up, so as to reflect different operating states of the micro-metering device. Based on this, the user can directly determine the current operating state of the micro-metering device by observing the color displayed by the reset button.

Described above are merely preferred embodiments of the present disclosure, and are not intended to limit the present disclosure. Though the disclosure has been described in detail above, those skilled in the art can still make various changes, substitutions and variations. It should be understood that those modifications, substitutions, and improvements made without departing from the spirit and principles of the present disclosure shall be included in the scope of the present disclosure defined by the appended claims.

What is claimed is:

1. A micro-metering device with a constant flow rate, comprising:
   a rotary shear valve;
   a mounting seat;
   a rotation drive assembly;
   an injection drive assembly; and
   a controller;
   wherein the rotary shear valve comprises a valve main body and a valve spool; the valve main body is provided with a main flow channel and a plurality of branch flow channels; and the valve spool is rotatably arranged inside the valve main body, and is configured to communicate the main flow channel with at least one of the plurality of branch flow channels;
   a pressure sensor is provided inside the valve main body, and is communicated with the main flow channel; and the pressure sensor is configured for detecting a pressure inside the main flow channel;
   the valve main body comprises a valve head cover, a valve head and a valve head housing arranged sequentially from one side to the other side, wherein the main flow channel and the plurality of branch flow channels are provided on the valve head;
   a first side of the valve head is provided with a mounting groove communicated with the main flow channel, and the mounting groove is configured to accommodate the pressure sensor; a sealing ring is provided between a first side of the pressure sensor and the mounting groove; and the valve head cover is configured to seal the mounting groove, and is detachably connected to the valve head;
   a lead wire of the pressure sensor is connected with a probe; and the probe passes through the valve head and the valve head housing successively and extends to an outside of the valve head housing;

the valve spool is rotatably arranged in an inner cavity of the valve head housing, and is located on a second side of the valve head; and a valve body is arranged between the valve head and the valve spool;

a valve spool base, a bearing and a disc spring are provided in sequence in the inner cavity of the valve head housing from one side to the other side; the valve spool base is rotatably provided in the inner cavity of the valve head housing via the bearing; the valve spool is fixedly arranged on a first side of the valve spool base; a sealing gasket is provided between the valve spool and the valve spool base; a connection port is provided on a second side of the valve spool base, and a through hole aligned with the connection port is provided on a side of the valve head housing; and a first end of the disc spring is connected to the bearing, and a second end of the disc spring is connected to the valve head housing;

the rotary shear valve is arranged on a first side of the mounting seat, and the rotation drive assembly, the injection drive assembly and the controller are arranged on a second side of the mounting seat;

the rotation drive assembly is configured to drive the valve spool to rotate; the injection drive assembly comprises an injector and an injection drive member; an output end of the injector is communicated with the main flow channel; the injection drive member is configured to drive the injector to realize liquid suction and discharge; and the pressure sensor, the rotation drive assembly and the injection drive member are electrically connected to the controller;

the injection drive member comprises an injection drive motor, a transmission component, a ball screw, a push plate and a linear encoder; the ball screw is rotatably arranged on a side of the mounting seat away from the rotary shear valve; the injection drive motor is in transmission connection with the ball screw through the transmission component, so that the ball screw is driven by the injection drive motor to rotate; the ball screw runs through the push plate and is threadedly connected to the push plate; the push plate is capable of sliding along an axial direction of the ball screw; the mounting seat is provided with an avoidance opening fitting the push plate; an input end of the injector is connected to the push plate; the linear encoder is configured to detect a position of the push plate; and the injection drive motor and the linear encoder are electrically connected to the controller;

the linear encoder comprises a code rail and a read head assembly; the code rail is fixedly provided on the push plate and is parallel to the ball screw; the read head assembly is fixedly provided on the mounting base, and is electrically connected to the controller; and during the liquid suction and discharge, the controller is configured to dynamically adjust an output power of the injection drive motor according to the pressure in the main flow channel detected by the pressure sensor.

2. The micro-metering device of claim 1, wherein a side of the valve head cover is provided with an abutting step; a side of the abutting step abuts against a second side of the pressure sensor; and the abutting step is provided with a notch for the lead wire of the pressure sensor to pass through.

3. The micro-metering device of claim 1, wherein the rotation drive assembly comprises a rotation drive motor, a rotary shaft, a zero-position code disk, a positioning code disk and a rotary photoelectric sensor;

the rotation drive motor is fixedly arranged on a side of the mounting seat away from the rotary shear valve; a first end of the rotary shaft is in transmission connection with the rotation drive motor, and a second end of the rotary shaft is in transmission connection with the valve spool; the zero-position code disk and the positioning code disk are both sleeved on an outer wall of the rotary shaft, and are coaxial with the rotary shaft; the rotary photoelectric sensor is arranged on a side of the rotary shaft, and is adapted to the zero-position code disk and the positioning code disk; and the rotation drive motor and the rotary photoelectric sensor are electrically connected to the controller.

4. The micro-metering device of claim 1, wherein the transmission component comprises a drive wheel, a driven wheel and a synchronous belt; the drive wheel is in transmission connection with an output end of the injection drive motor; the driven wheel is sleeved on an outer wall of the ball screw, and is coaxial with the ball screw; and the drive wheel and the driven wheel are in transmission connection through the synchronous belt.

5. The micro-metering device of claim 1, wherein the injection drive member comprises two guide columns; the two guide columns are symmetrically arranged on two sides of the ball screw, and are parallel to the ball screw; and each of the two guide columns runs through the push plate, and is slidably connected to the push plate.

* * * * *